United States Patent [19]

Brewer

[11] 4,287,306

[45] Sep. 1, 1981

[54] APPARATUS FOR GENERATION OF ANAEROBIC ATMOSPHERE

[75] Inventor: John H. Brewer, Abilene, Tex.

[73] Assignee: Becton, Dickinson and Company, Paramus, N.J.

[21] Appl. No.: 26,337

[22] Filed: Apr. 2, 1979

[51] Int. Cl.³ .............................. B01J 7/00; B01J 8/02; C12M 1/00

[52] U.S. Cl. ...................................... 435/287; 422/86; 422/119; 422/222; 422/238; 422/239; 435/801

[58] Field of Search .............. 422/236, 238, 239, 222, 422/119, 57, 86, 87; 435/287, 801

[56] References Cited

U.S. PATENT DOCUMENTS

| | | | |
|---|---|---|---|
| 2,418,175 | 4/1947 | Higginbotham | 252/472 |
| 3,246,959 | 4/1966 | Brewer | 422/236 |
| 3,419,400 | 12/1968 | Hayhurst et al. | 422/222 |
| 3,483,089 | 12/1969 | Brewer | 435/287 |
| 3,652,317 | 3/1972 | Della Porta et al. | 427/194 |
| 3,890,104 | 6/1925 | Porta et al. | 422/222 |
| 3,891,509 | 6/1975 | Warren et al. | |
| 4,003,709 | 1/1977 | Eaton et al. | 422/86 |
| 4,013,422 | 3/1977 | Spinner et al. | 422/236 |
| 4,014,748 | 3/1977 | Spinner et al. | |
| 4,023,934 | 5/1977 | Spinner et al. | 422/86 |
| 4,038,148 | 7/1977 | Miller et al. | |
| 4,108,728 | 8/1978 | Spinner et al. | |

OTHER PUBLICATIONS

"Condensed Chem. Dictionary"; 8th Ed.; 1971; p. 881.
The Merck Index; 9th Ed.; 1976; S1815; pp. 230 & 231.

Primary Examiner—Bradely Garris

[57] ABSTRACT

A gas generating package includes tablets or other material, which when contacted with water generates both hydrogen and carbon dioxide. A catalyst for the hydrogen-oxygen reaction is applied to the exterior of the package, with the exterior of the package preferably also having applied thereto carbon dioxide and anaerobic indicators. In this manner fresh material is employed during each run requiring an anaerobic atmosphere.

10 Claims, 3 Drawing Figures

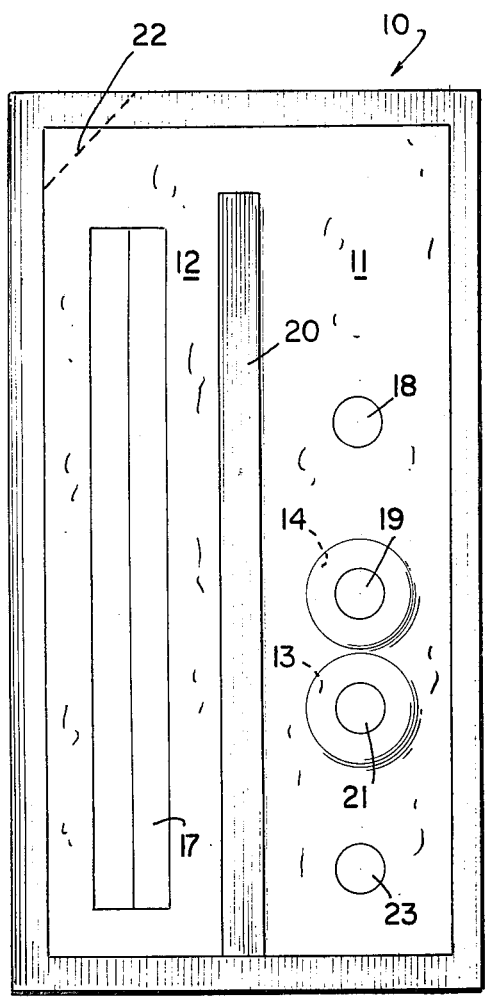
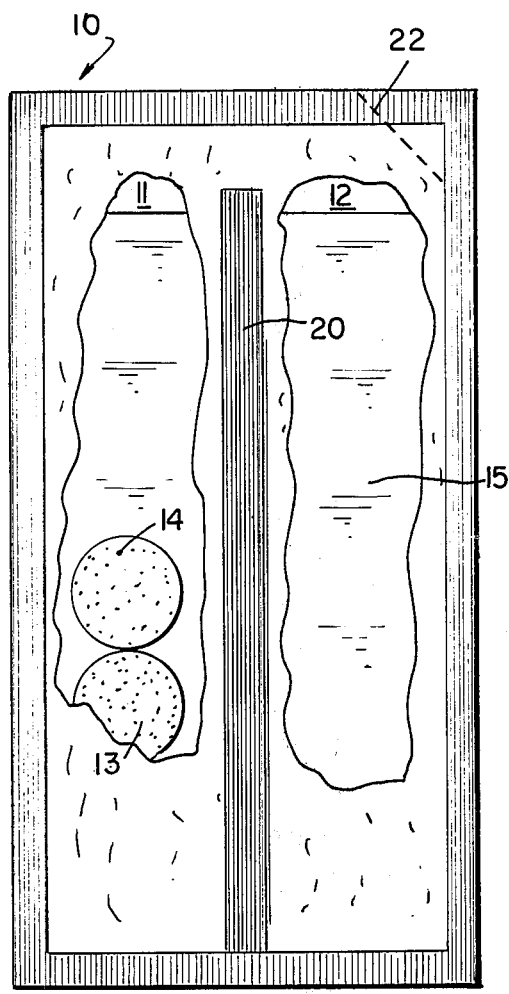

APPARATUS FOR GENERATION OF ANAEROBIC ATMOSPHERE

This invention relates to gas generation, and more particularly to the generation of an anaerobic atmosphere.

Anaerobic atmospheres are required for the culturing of some microorganisms. U.S. Pat. No. 3,246,959 discloses an apparatus for generating such anaerobic atmosphere and U.S. Pat. No. 3,483,089 discloses anaerobic apparatus for anaerobic culturing, which includes a cold platinium catalyst. In accordance with U.S. Pat. No. 3,246,959, there is provided a package which includes, for example, a material which is capable of generating hydrogen upon being contacted with water. The interior of the package is divided into two compartments, which are in fluid flow communication with each other, with one of the compartments including the hydrogen generating material. Upon introducing water into the other compartment, there is a controlled flow of water into the compartment containing the hydrogen generating material. Such package can be employed in an anaerobic jar such as disclosed in U.S. Pat. No. 3,483,089.

The present invention is directed to an improvement in such gas generating devices.

In accordance with the present invention, there is provided an article for producing an atmosphere for use in providing an anaerobic atmosphere comprised of a package, the interior of which includes a material which is capable of evolving a gas which reacts with gaseous oxygen, and the exterior of which includes a catalyst for catalyzing reaction between oxygen and the gas generated within and released from the package.

In accordance with a preferred embodiment, the interior of the package includes a material, preferably in the form of a tablet, which is capable of generating hydrogen, with a catalyst for the oxygen-hydrogen reaction being applied to the exterior of the package. In accordance with a particularly preferred embodiment, the interior of the package also includes a material, also preferably in the form of a tablet, which is capable of generating carbon dioxide. In accordance with another preferred aspect of the present invention, the exterior of the package also has applied an anaerobic indicator(s) in order to show that anaerobiosis of a proper level has been achieved and a carbon dioxide indicator to indicate that the required carbon dioxide level has been achieved.

In accordance with another aspect of the present invention, there is provided a new and improved carbon dioxide generating composition. More particularly, the composition is formulated in a manner to generate carbon dioxide and provide an acidic pH whereby when used in a gas generating package along with a hydrogen generator acidic conditions are maintained to thereby prevent carbon dioxide absorption which may occur under alkaline conditions.

More particularly, the composition includes a water soluble solid acid and a water soluble solid carbonate in amounts suitable for generating carbon dioxide and also providing an acidic pH; in particular, in general, a pH of less than 6 when dissolved in water. As representative examples of suitable acids, there may be mentioned: citric, tartaric, ascorbic, succinic, maleic, fumaric, lactic acids and the like. As representative examples of suitable carbonates, there may be mentioned; sodium bicarbonate, sodium carbonate, potassium carbonate, sodium sesquicarbonate, etc. The preferred composition includes citric acid and sodium bicarbonate. The composition is preferably employed in the form of a tablet in which case suitable lubricants and binders are generally also employed. The exact proportions of acid and carbonate will differ with the materials used. The selection of suitable amounts to provide the desired carbon dioxide concentration for culturing and the acidic pH is deemed to be within the scope of those skilled in the art from the teachings herein.

The invention will be further described with respect to a preferred embodiment thereof; however, it is to be understood that the scope of the invention is not to be limited thereby. Such a preferred embodiment is illustrated in the accompanying drawings, wherein:

FIG. 1 is an elevational view of a preferred embodiment of a gas generating device in accordance with the invention;

FIG. 2 is a cross-sectional view of the device of FIG. 1; and

Figure 3:
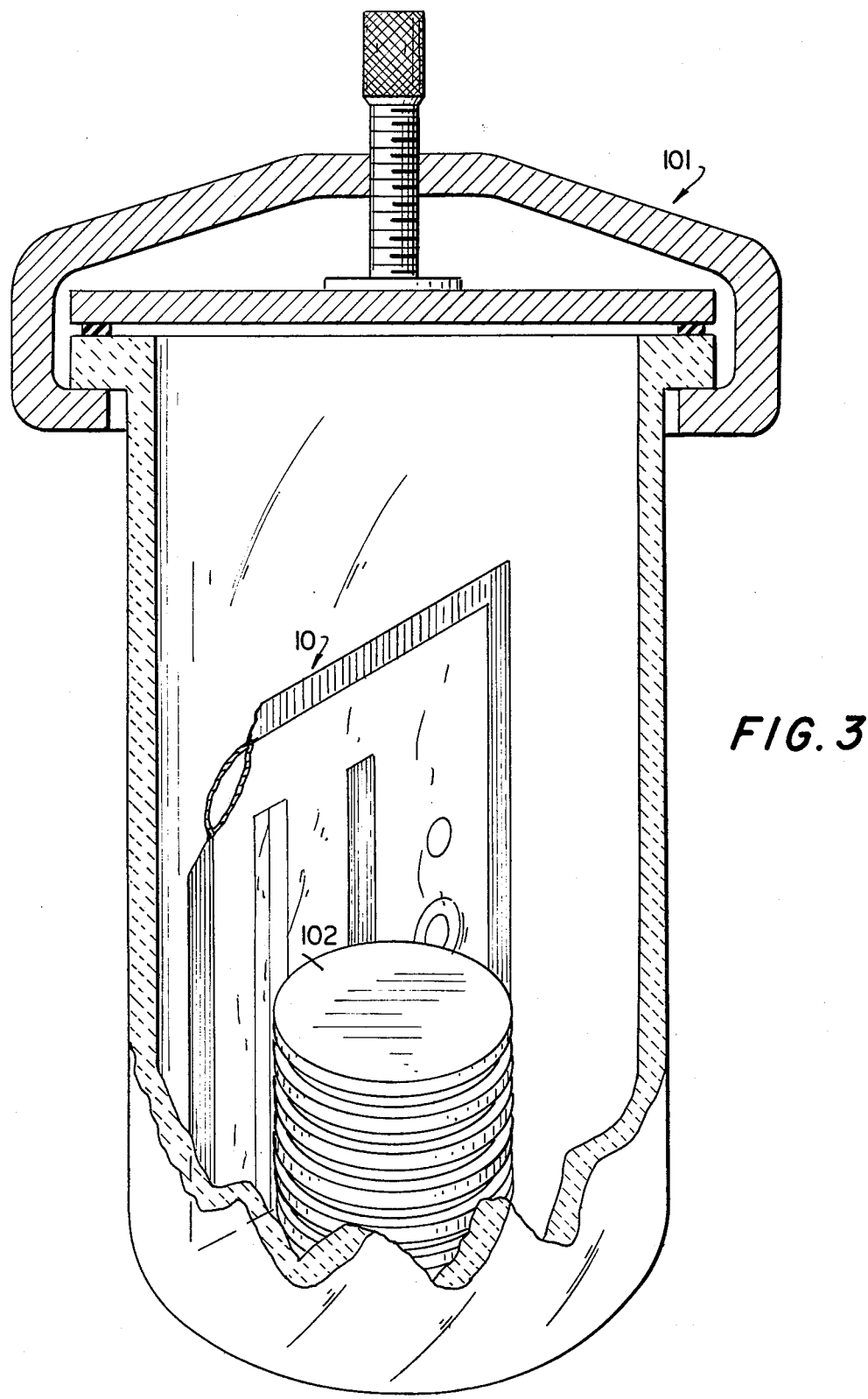
FIG. 3 is an elevational view of an anaerobic jar employing the gas generating device.

Referring now to the drawings, there is shown a device for generating an anaerobic atmosphere comprised of a package in the form of an envelope 10 made of a suitable material which is impervious to the atmosphere and moisture, and which is inert to materials contained within the package and gases generated therein and which is not destroyed by the heat of reaction released during use of the package, as hereinafter described. Thus, for example, the envelope 10 may be formed of a metallic foil, such as aluminum which is coated on its inner surface with a thermoplastic material, such as polyethylene or a polymer formed of vinyl chloride. The envelope 10 may be formed from two panels suitably secured together around the edges by heat sealing. The interior of the envelope is divided into a first gas generating compartment 11 and a second liquid-receiving compartment 12 by a suitable partition 20 formed, for example, by heat sealing. The compartment 11 includes gas generating material in the form of a tablet 13, which includes materials capable of generating hydrogen and a tablet 14, which includes materials capable of generating carbon dioxide. The interior compartments 11 and 12 are in internal fluid flow communication with each other through a fluid transfer means in the form of, for example, filter paper 15 which is capable of permitting both liquid and gas flow between compartments 11 and 12. The filter paper 15 extends through the partition 20 into each of the compartments 11 and 12. As a result of the porosity of the filter paper, liquid and gas can slowly diffuse between the internal compartments. It is to be understood, however, that other porous material such as blotting paper, cotton twill, etc., may be employed instead of the filter paper 15. It is also to be understood that although the filter paper is shown as being a single sheet, it may be divided into two or more sheets. It is also to be understood that the package need not be restricted to two compartments. As particularly shown, the partition 20 terminates before the top of the package whereby the compartments are in communication with each other above the partition. The package is designed to be used in a manner such that liquid introduced into compartment 12 does not reach a level above the partition whereby compartments 11 and 12 are only in gas flow communication above the partition.

In accordance with the present invention, the exterior of package 10 is provided with a catalyst for catalyzing the reaction between oxygen and the hydrogen generated within and released from the package 10. As particularly shown, such catalyst is coated on the metallic foil forming the exterior of package 10, with such catalyst generally being indicated as 17. It is to be understood that the catalyst could be applied other than by coating. In particular, such a catalyst could be comprised of palladium or platinum, supported on a suitable support, such as carbon, aluminum oxide or other metal oxides which is then coated or otherwise applied onto the exterior of the package. Although the catalyst is generally shown in the form of stripes, it is to be understood that the catalyst may be applied in another form.

The catalyst is applied to the exterior of the package in an amount sufficient for catalyzing the reaction between hydrogen and oxygen to thereby generate an anaerobic atmosphere. Although the catalyst is generally coated on the exterior of the package, other methods of application are possible; for example, providing the exterior of the package with an adhesive and dusting the catalyst. In coating or otherwise applying the catalyst to the package exterior, the application should be effected in a manner such that the other materials employed, such as coating materials, do not "mask" the catalyst. The particular means for applying the catalyst to the package exterior is deemed to be within the scope of those skilled in the art from the teachings herein.

The catalyst may be applied to the package in a wide variety of forms and in a wide variety of locations. In some cases, if the catalyst is applied as a concentrated spot over the tablet, scorching of the package may occur, which should be avoided to prevent possible contamination. The specific arrangement of the catalyst to achieve optimum results is well within the scope of those skilled in the art from the teachings herein.

In accordance with a particularly preferred embodiment, an anaerobic indicator is also applied to the exterior of package 10. Such an indicator may be coated or otherwise applied to the metallic foil, and such indicator, as particularly shown, is in the form of three different indicators, generally indicated as 18, 19 and 21. The indicators may be of methylene blue, resazurin, and indigo carmine which respond to different levels of oxygen, or which have different oxidation—reduction potentials. The use of such indicators will indicate different levels of oxygen. A similar indicator for monitoring the level of carbon dioxide is also applied to the external surface of the metallic foil and is generally indicated as 23. Although such indicators have been particularly shown as being printed as spots on the exterior of the package, it is to be understood that the indicator may take other forms such as lettering or other designs.

As should be apparent, the package forms an integral unit for providing an anaerobic atmosphere in that the package includes the materials for generating hydrogen and carbon dioxide, as well as the catalyst for catalyzing the reaction between hydrogen and oxygen and the indicators for indicating anaerobic conditions and carbon dioxide concentration.

In employing the gas generating device of the present invention, the liquid receiving compartment 12 is opened by cutting away or tearing a corner of the package 10 along a tear line, generally indicated as 22. A material capable of interacting with the gas generating materials in compartment 11, such as water, is introduced into compartment 12, and such water flows into compartment 11, at a controlled rate, through the filter paper 15. Upon contact with water, the tablets 13 and 14 generate hydrogen and carbon dioxide, which flows from compartment 11 into compartment 12 through the filter paper 15 and/or through the open upper channel, and ultimately into the container in which the envelope has been placed. The hydrogen reacts with oxygen in such container, with such reaction being catalyzed by the catalyst 17 applied to the exterior of package 10. In addition, anaerobic conditions are indicated by means of the indicators 18, 19 and 21 which are also applied to the exterior of package 10. Carbon dioxide concentration is indicated by indicator 23 which is also applied to the exterior of the package.

The invention will be described with respect to the following example; however, the scope of the invention is not to be limited thereby:

EXAMPLE

The following exemplifies a package in accordance with the present invention, which includes a carbon dioxide generating tablet, a hydrogen generating tablet, a catalyst for the reaction between hydrogen and oxygen applied to the exterior of the package and anaerobic and carbon dioxide indicators applied to the exterior of the package. The package in accordance with the example is employed as a gas generator, with such gas generation being effected by the addition of 10 ml of water to the liquid receiving compartment.

CARBON DIOXIDE GENERATING TABLET

Citric Acid, 1.850 gm
Sodium Bicarbonate, 0.730–0.820 gm

In addition, the tablet includes suitable binder and lubricant; e.g., 0.1 g boric acid and 0.015 g magnesium stearate.

HYDROGEN GENERATING TABLET

Sodium Borohydride, 0.9 gm

The tablet includes suitable binder and lubricants. Optionally, the tablet can include 0.2 gm of nickel or cobalt as catalyst. The tablet can be coated with a water soluble gelatin to prevent decomposition.

FORMULATION OF CATALYST COATING 0.3333 g. of Gum of Tragacanth
1.2 g. of 5% carbon palladium catalyst
Boil, cool and then shake mixture for uniformity.

FORMULATION OF INDICATOR BASE 18 g. fructose
1.53 g. $K_2HPO_4$
0.35 g. NaOH
2.5 mg. phenyl mercuric nitrate

FORMULATION OF METHYLENE BLUE INDICATOR

Indicator base
5 mg methylene blue
Weigh 1.2 g. of dry indicator mixture with 0.3333 g. Gum of Tragacanth. Add 40 ml. of water and boil. Cool, ready for use.

FORMULATION OF INDIGO CARMINE INDICATOR

Indicator base 5 mg indigo carmine
Weight 1.2 g. of dry indicator mixture with 0.3425 g. Gum of Tragacanth. Mix with 40 ml. of water and boil. Cool, ready for use.

FORMULATION OF RESAZURIN INDICATOR

Indicator base
5 mg. of resazurin
Weight 1.2 g. of dry indicator preparation with 0.3345 g. Gum of Tragacanth.
Add 40 ml. of water and boil. Cool, ready for use.

FORMULATION OF CARBON DIOXIDE INDICATOR

Sodium Bicarbonate, 0.02 g.
Brom Thymol Blue, 0.001 g.
Gum of Tragacanth, 0.3333 g.
Mix with 40.0 ml. of water and boil. Cool, ready for use.

APPLICATION OF CATALYST

Apply sufficient catalyst coating to foil exterior to provide at least 0.001 g of palladium catalyst. Dry the stripe. The catalyst is ready to use.

APPLICATION OF INDICATOR

Methylene blue—Apply 1 drop (0.05 cc.) of indicator to exterior aluminum surface of package and dry.
Indigo carmine—Apply 1 drop (0.05 cc.) of indicator to exterior aluminum surface of package and dry.
Resazurin—Apply 1 drop (0.05 cc.) of indicator to exterior aluminum surface of package and dry.

Although the invention has been described with respect to a preferred embodiment thereof, it is to be understood that numerous modifications are possible with the scope of the invention. Thus, for example, a liquid other than water could be employed for generating the gas, and tablets other than those particularly described could also be employed for generating gas. Thus, for example, a tablet capable of generating acetylene could be employed instead of a hydrogen generating tablet, although a hydrogen generating tablet is preferred. Similarly, the tablet could be formulated for producing hydrogen in a manner other than as particularly described; e.g., hydrogen could be generated by another liquid, such as an acid; in particular, hydrochloric acid, although the use of water is preferred. Similarly, the liquid for generating the gas upon contacting the tablet could be within the package in a separate compartment or ampoule. Thus, the present invention is not limited to the particularly described embodiment in that it is possible to provide a package which includes a material for generating hydrogen within the package, and a catalyst on the exterior of the package in configurations other than the one particularly described.

The present invention is particularly advantageous in that it is no longer necessary to employ a specific type of container or jar for generating anaerobic conditions in that the gas generating package is self contained; i.e., the package contains the material for generating the gas, as well as catalyst and indicator. Moreover, the present invention provides for fresh catalyst each time a run is made, thereby eliminating the previous problem of catalyst poisoning from a previous run. Moreover, the heat of reaction from the tablet is transferred through the package and activates the catalyst more rapidly than the cold catalyst in the lid of the jar heretofore employed in the art. Simultaneously, heat generated by the catalyst increases the rate of reaction for the tablets. Furthermore, in accordance with a preferred embodiment, the anaerobic indicator is provided on the package thereby eliminating the necessity of adding a separate indicator.

Thus, for example, as shown in FIG. 3 the gas generating package 10 is employed in an anaerobic jar 101 including culture plates 102 and such jar does not include a cold catalyst for the oxygen-hydrogen reaction or a separate indicator.

In addition, the carbon dioxide generating tablet in accordance with the present invention is an improvement over the prior tablets because the tablet produces an acid pH during gas generation within the package and thereby inhibits carbon dioxide absorption which could occur under alkaline conditions. In addition, such tablets are capable of providing an atmosphere of 7.5 to 8.5% carbon dioxide even after 24 hours.

These and other advantages should be apparent to those skilled in the art from the teachings herein.

Numerous modifications and variations of the present invention are possible in light of the above teachings and, therefore, within the scope of the appended claims, the invention may be practised otherwise than as particularly described.

I claim:
1. A unitary package for generating an anaerobic atmosphere for use in culturing anaerobic microorganisms, characterized by
   (a) a flexible sealed package;
   (b) material in said package for generating hydrogen;
   (c) material in said package for generating carbon dioxide; and
   (d) a catalyst coated onto the exterior surface of said flexible sealed package;
   (e) whereby when said package is broken and water is inserted to react with said hydrogen generating material said externally coated catalyst catalyzes the reaction between oxygen outside said package and the said generated hydrogen.
2. The package of claim 1, further characterized by
   (a) said flexible sealed package is metallic foil.
3. The package of claim 1, further characterized by
   (a) an anaerobic indicator applied to the exterior of said flexible sealed package.
4. The package of claim 1, further characterized by
   (a) a carbon dioxide indicator applied to the exterior of said flexible sealed package.
5. The package of claim 1, further characterized by
   (a) a first interior compartment;
   (b) a second interior compartment;
   (c) said first interior compartment containing said hydrogen and said carbon dioxide generating materials;
   (d) said second compartment containing a frangible portion for inserting water; and
   (e) a porous segment between said first and second compartment causing flow communication therebetween.
6. The package of claim 1, further characterized by
   (a) said material for generating carbon dioxide is a water soluble solid carbonate and a water soluble solid acid for providing an acidic pH in the generated gas in said package.
7. The package of claim 1, further characterized by
   (a) said material for generating hydrogen is sodium borohydride.
8. The package of claim 1, further characterized by

(a) said coated catalyst is selected from the group consisting of supported palladium and supported platinum.

9. The package of claim 1, further characterized by said coated catalyst comprising (a) carbon palladium catalyst and wherein said catalyst is coated on said package exterior with Gum of Tragacanth.

10. The package of claim 9, further characterized by (a) said carbon palladium catalyst being present in said catalyst coating in an amount of at least 0.001 grams.

* * * * *